United States Patent
Abe et al.

(10) Patent No.: US 10,028,796 B1
(45) Date of Patent: Jul. 24, 2018

(54) OPERATIONAL FEELING REPRODUCTION DEVICE

(71) Applicant: TORAY ENGINEERING CO., LTD., Chuo-ku, Tokyo (JP)

(72) Inventors: Tetsuya Abe, Otsu (JP); Chisa Inaka, Otsu (JP)

(73) Assignee: TORAY ENGINEERING CO., LTD., Tokyo (JP)

( * ) Notice: Subject to any disclaimer, the term of this patent is extended or adjusted under 35 U.S.C. 154(b) by 0 days.

(21) Appl. No.: 15/745,614

(22) PCT Filed: Jul. 19, 2016

(86) PCT No.: PCT/JP2016/071102
§ 371 (c)(1),
(2) Date: Jan. 17, 2018

(87) PCT Pub. No.: WO2017/022466
PCT Pub. Date: Feb. 9, 2017

(30) Foreign Application Priority Data

Aug. 4, 2015 (JP) .................................. 2015-154354

(51) Int. Cl.
*H04B 3/36* (2006.01)
*A61B 34/00* (2016.01)
(Continued)

(52) U.S. Cl.
CPC ............... *A61B 34/76* (2016.02); *G05G 5/03* (2013.01); *G09B 23/285* (2013.01)

(58) Field of Classification Search
CPC ......... A61B 34/76; G05G 5/03; G09B 23/285
(Continued)

(56) References Cited

U.S. PATENT DOCUMENTS 6,096,004 A * 8/2000 Meglan .................. A61B 34/75
604/95.01
6,375,471 B1 4/2002 Wendlandt et al.
(Continued)

FOREIGN PATENT DOCUMENTS

JP 2000-042117 A 2/2000
JP 2000-181618 A 6/2000
(Continued)

OTHER PUBLICATIONS

Ide et al., Development of Master Slave System for Interventional Radiology with Force-Rate Control, Journal of the Robotics Society of Japan, Mar. 15, 2010, pp. 91 to 98, vol. 28, No. 2, Robotics Society of Japan, Japan.
(Continued)

*Primary Examiner* — Ojiako Nwugo
(74) *Attorney, Agent, or Firm* — Global IP Counselors, LLP

(57) ABSTRACT

An operational feeling reproduction device includes an operation component, an actuator, and a drive shaft. The actuator generates a haptic drive force in response to operation of the operation component. The drive shaft couples the operation component and the actuator. The haptic drive force is transmitted to the operation component through the drive shaft in response to the operation of the operation component such that an actual operational feeling is experienced. The actuator has a stationary element and a movable element. The actuator generates the haptic drive force by a relative displacement while one of the stationary element and the movable element is inserted into the other one of the stationary element and the movable element. The movable element and the operation component are coupled by the drive shaft. Center axes of the stationary element, the
(Continued)

movable element, and the drive shaft are provided on the same axis.

16 Claims, 5 Drawing Sheets

(51) Int. Cl.
    *G05G 5/03*     (2008.04)
    *G09B 23/28*     (2006.01)

(58) Field of Classification Search
    USPC .......................................... 340/407.1, 407.2
    See application file for complete search history.

(56) References Cited

U.S. PATENT DOCUMENTS

| | | | | |
|---|---|---|---|---|
| 6,470,302 | B1* | 10/2002 | Cunningham | ......... G09B 23/28 |
| | | | | 128/897 |
| 6,929,481 | B1 | 8/2005 | Alexander et al. | |
| 8,610,548 | B1* | 12/2013 | Provancher | .............. H04B 3/36 |
| | | | | 340/407.1 |
| 8,981,914 | B1* | 3/2015 | Stetten | ................... A61B 42/10 |
| | | | | 340/407.1 |
| 2001/0016804 | A1 | 8/2001 | Cunningham et al. | |
| 2003/0069719 | A1 | 4/2003 | Cunningham et al. | |
| 2004/0045561 | A1 | 3/2004 | Alexander et al. | |
| 2004/0048230 | A1 | 3/2004 | Alexander et al. | |
| 2004/0076940 | A1 | 4/2004 | Alexander et al. | |
| 2006/0046235 | A1 | 3/2006 | Alexander et al. | |
| 2010/0041991 | A1* | 2/2010 | Roundhill | ............ A61B 8/4281 |
| | | | | 600/443 |
| 2012/0219937 | A1* | 8/2012 | Hughes | ................ G09B 23/285 |
| | | | | 434/268 |
| 2015/0130599 | A1* | 5/2015 | Berkley | ................... G08B 6/00 |
| | | | | 340/407.2 |

FOREIGN PATENT DOCUMENTS

| | | |
|---|---|---|
| JP | 2002-502058 A | 1/2002 |
| JP | 3872210 B2 | 1/2007 |
| JP | 2010-015164 A | 1/2010 |

OTHER PUBLICATIONS

International Search Report of the corresponding International Application No. PCT/JP2016/071102, dated Oct. 4, 2016.

* cited by examiner

OPERATIONAL FEELING REPRODUCTION DEVICE

This application is a U.S. National stage of International Application No. PCT/JP2016/071102 filed on Jul. 19, 2016. This application claims priority to Japanese Patent Application No. 2015-154354 filed with Japan Patent Office on Aug. 4, 2015. The entire disclosure of Japanese Patent Application No. 2015-154354 is hereby incorporated herein by reference.

BACKGROUND

Field of the Invention

The present invention relates to an operational feeling reproduction device, which is a simulation device for experiencing the actual operational feeling, and with which experiments, training, and the like can be carried out by reproducing a simulation of the operational feeling, without using the real object.

Background Information

A simulation device (operational feeling reproduction device) is used to transmit the tactile feeling and operational feeling felt by a person to a person who has never experienced those feelings before, and to develop a real sense by learning these feelings. For example, in the field of surgery, intravascular treatment is performed by using a medical catheter to send an intravascular dilation stent/balloon or an occlusion coil, and an operational feeling reproduction device is used in order to develop an operational feeling of this catheter.

As shown in FIG. 5, this operational feeling reproduction device has an operation component 100 that is operated by the user, an actuator 101 that generates a haptic drive force, a drive shaft 102 that links the operation component 100 and the actuator 101, and a controller 103 that comprehensively controls these, and is configured so that an image of the state when a catheter has actually been inserted into a human body, the operation situation, or the like is displayed on a monitor 104 from the controller 103. Then, the device is controlled so that the haptic drive force (tactile feeling) that would be experienced by a skilled physician is generated by the actuator 101 according to the amount of displacement inputted when the user operates the operation component 100, and the haptic drive force corresponding to the operation of the operation component 100 is transmitted to the operation component 100 through the drive shaft 102.

More specifically, a servomotor 105 is used for the actuator 101, for example, and when the user operates the operation component 100 while looking at the monitor 104, the amount of displacement of the drive shaft 102 is sensed by an encoder 106. A drive force corresponding to this displacement amount is then outputted from the servomotor 105. That is, the drive force of the servomotor 105 controlled by the controller 103 is transmitted through an intermediate member 107 to the drive shaft 102, and the user can obtain a tactile feeling that reflects the operation of the operation component 100 through the drive shaft 102. This makes it possible for physicians with no real surgical experience to experience light and delicate tactile feelings, such as how it feels when a catheter hits the wall of a blood vessel, or how it feels to form a balloon in a blood vessel, without actually practicing on a human body (see Japanese Patent Application Publication No. 2000-42118, for example).

SUMMARY

However, a problem with the above-mentioned operational feeling reproduction device is how difficult it is to accurately obtain an actual tactile feeling. That is, with a conventional operational feeling reproduction device, the center axis 1a of the drive source (servomotor 105) that generates the haptic drive force of the actuator 101 is located at a position that is offset with respect to the drive shaft 102 (center axis 1b) linked to the operation component 100, which means there is a risk that the accuracy of the haptic drive force generated by the actuator 101 may be impaired. More specifically, a problem has been that even when the haptic drive force generated by the actuator 101 is adjusted to the light and delicate haptic drive force felt by an experienced physician in response to the operation of the operation component 100, because the center axis 1a of the drive source and the center axis 1b of the drive shaft 102 are offset from each other, an unnecessary moment is generated and any mechanical loss, such as in the fitting accuracy and assembly precision of the intermediate member 107, that exists between the center axis 1a of the drive source and the center axis 1b of the drive shaft 102 will affect the haptic drive force, so that the haptic drive force transmitted to the operation component 100 will deviate slightly and not be accurately transmitted to the user who is operating the operation component 100.

The present invention was conceived in light of the above problems, and it is an object thereof to provide an operational feeling reproduction device with which a haptic drive force can be accurately transmitted, and a light and delicate tactile feeling can be developed.

In order to solve the stated problem, the operational feeling reproduction device of the present invention comprises an operation component that is operated by a user, an actuator that generates a haptic drive force in response to operation of the operation component, and a drive shaft that couples the operation component and the actuator, the haptic drive force generated by the actuator being transmitted to the operation component through the drive shaft in response to operation of the operation component such that an actual operational feeling is experienced, the actuator having a stationary element and a movable element, and generating the haptic drive force by a relative displacement while one is inserted into the other, and the movable element and the operation component being coupled by the drive shaft, and center axes of the stationary element, the movable element, and the drive shaft being provided on the same axis.

With this operational feeling reproduction device, the stationary element and the movable element of the actuator are formed by inserting one of them into the other, and the center axes of the stationary element, the movable element, and the drive shaft are provided on the same axis, so the haptic drive force can be faithfully reproduced and accurately transmitted. That is, since the respective center axes of the stationary element, the movable element, and the drive shaft are provided on the same axis, the drive shaft can drive at a lower resistance, with sliding resistance kept to a minimum, so a haptic drive force adjusted to be the light and delicate haptic drive force a skilled physician would feel can be accurately reproduced. Also, since there is no intermediate member interposed between the drive source and the drive shaft as in the past, it is possible to suppress the influence of the moment attributable to an offset structure and to mechanical loss such as in fitting accuracy and assembly precision, and the problem of the haptic drive force transmitted to the operation component deviating slightly can be minimized. Therefore, compared to a conventional operational feeling reproduction device in which the center axis of the drive source is offset from the center axis of the drive shaft, it is possible to transmit the haptic drive force set by the actuator more accurately, so the user can develop a light and delicate tactile feeling.

Also, a plurality of actuators are provided, and the drive shaft coupled to the movable element of each of the actuators being each coupled to the operation component, each drive shaft shares a common center axis, one drive shaft being inserted into another drive shaft, and the center axes of the drive shaft, and the stationary element and the movable element of each of the actuators are provided on the same axis.

With this configuration, even if a plurality of actuators generate a haptic drive force, it is possible to dispose the center axes of the drive shaft, the stationary element and the movable elements of each on the same axis, so compared to a conventional operational feeling reproduction device in which the center axis of the actuator, which is the drive source, is offset from the center axis of the drive shaft, the drive shaft can be driven at a lower resistance, with sliding resistance kept to a minimum, and furthermore there will be no need for space in a direction perpendicular to the center axes, affording a device that is more compact overall.

Also, it is preferable if the actuator is a non-contact drive motor in which the movable element and the stationary element are relatively displaced in a non-contact manner.

With this configuration, compared to when a mechanical driving source such as a ball screw or a servomotor is used for the actuator, the influence of loss, vibration, and the like peculiar to a mechanical drive source, such as sliding resistance or pulsation, can be eliminated, so a haptic drive force that is closer to the real thing can be accurately reproduced and transmitted.

Also, the configuration may be such that an insertion hole through which the movable element is inserted is formed in the stationary element, and an air bearing for supporting the movable element in a non-contact manner is provided to the insertion hole. With this configuration, since the movable element is supported in a non-contact manner with respect to the stationary element, the influence of sliding resistance when the movable element and the stationary element move relative to each other can be eliminated, and a haptic drive force that is closer to the real thing can be accurately reproduced and transmitted.

Also, the configuration may be such that the haptic drive force generated by the actuator is generated in response to an operation of moving the drive shaft in the center axis direction and an operation of rotating the drive shaft around the center axis. With this configuration, it is possible for the user to develop a tactile feeling that is a combination of the operation of moving the operation component in the center axis direction and the operation of rotating the operation component around the center axis. That is, since the respective center axes of the stationary element, the movable element, and the drive shaft are provided on the same axis, the influence of moment, mechanical loss, and so forth can be suppressed, and drive can be performed with low resistance in both the center axis direction and the around the center axis, so a haptic drive force that has been adjusted to the light and delicate haptic drive force felt by a skilled physician can be accurately reproduced.

With the operational feeling reproduction device of the present invention, it is possible to accurately transmit a haptic drive force, and to develop a light and delicate tactile feeling.

DETAILED DESCRIPTION OF EMBODIMENTS

An embodiment of the operational feeling reproduction device of the present invention will be described through reference to the drawings.

Figure 1:
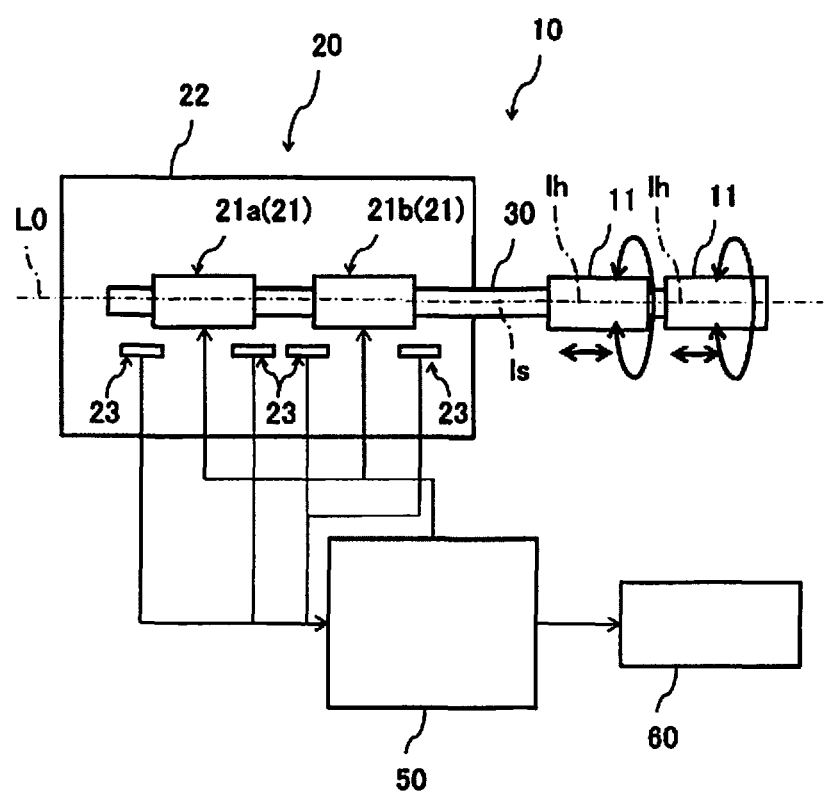
FIG. 1 is a diagram of the operational feeling reproduction device in an embodiment of the present invention.
Figure 2:
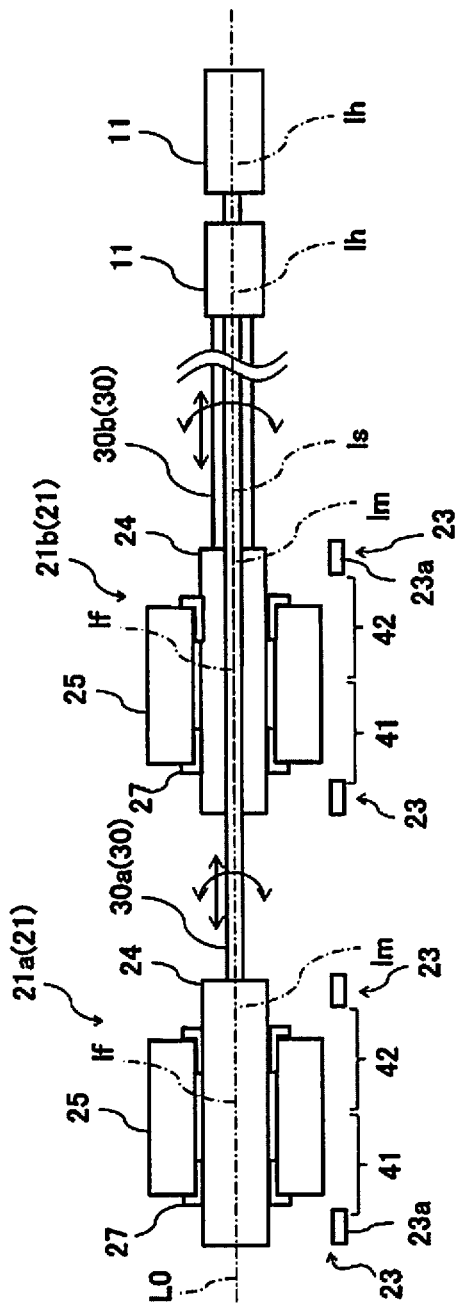
FIG. 2 is a diagram of a main part (device main body) in the embodiment.

FIG. 1 is an overall view showing an embodiment of an operational feeling reproduction device, and FIG. 2 is a diagram of the main part (device main body) of the operational feeling reproduction device. In the following embodiment, an example of applying the operational feeling reproduction device to a trainer (training machine) for a medical catheter will be described, but the operational feeling reproduction device of the present invention can be applied to any simulation device for obtaining a light and delicate tactile feeling, such as a surgical robot or a virtual reality system with which remote operation is required.

In FIGS. 1 and 2, the operational feeling reproduction device has a device main body 10 that generates a haptic drive force, a controller 50 that comprehensively controls the device main body 10, and a monitor 60 that receives signals from the controller 50 and monitors the usage state of the device main body 10. Then, when the user operates the device main body 10 (a catheter in this embodiment), the monitor 60 displays an image of the catheter actually inserted into a human body and an image of a state corresponding to the operation by the user, and a haptic drive force corresponding to the actual operation is transmitted to the user through the device main body 10 such that the user can experience the actual operational feeling.

The device main body 10 has an operation component 11 that is operated by the user, an actuator 20 that generates a haptic drive force, and a drive shaft 30 that couples the operation component 11 and the actuator 20.

The operation component 11 is a portion for the user to grasp and operate by hand, and the user operates it while looking at the monitor 60. The operation component 11 is substantially cylindrical in shape and is formed in substantially the same shape as the actual operational portion of a catheter. The actuator 20 in this embodiment is provided with two actuators 21, as discussed below, so one operation component 11 is independently provided for each.

The drive shaft 30 is formed by a rod-like member extending in one direction, one end of which is linked to the actuator 20 and the other is linked to the operation component 11. The operation component 11 and the drive shaft 30 are coupled so that they share a common axis (the center axis L0). More specifically, the operation component 11 and the drive shaft 30 are linked so that the center axis $1h$ of the operation component 11 and the center axis $1s$ of the drive shaft 30 are on the same axis (on the center axis L0), so when the operation component 11 is displaced along the center axis $1h$, the drive shaft 30 is displaced in the direction of the center axis L0 with respect to the actuator 20, and when the operation component 11 is displaced around the center axis 1h, the drive shaft 30 is displaced (rotated) around the center axis L0 with respect to the actuator 20.

In this embodiment, there are two actuators 21 and two drive shafts 30. The two drive shafts 30 are independently provided, one each to the actuators 21a and 21b. That is, there are provided a drive shaft 30a (see FIG. 2) linked to the actuator 21a located farther away from the operation component 11, and a drive shaft 30b (see FIG. 2) linked to the actuator 21b located closer to the operation component 11. These drive shafts 30a and 30b are configured so that their center axes 1s are on the same axis (on the center axis L0). More specifically, the drive shaft 30a is inserted through the drive shaft 30b, and the center axis 1s of the drive shaft 30a is disposed on the same axis as the center axis 1s of the drive shaft 30b, and the drive shaft 30a able to rotate in the center axis L0 direction and around the center axis L0 with respect to the drive shaft 30b. That is, when the operation component 11 is operated, the drive shaft 30a and the drive shaft 30b are independently displaced in the direction of the center axis L0, and rotate around the center axis L0, in a state of sharing a common center axis L0. That is, the drive shaft 30a and the drive shaft 30b can rotate in the center axis L0 direction and around the center axis L0 with less resistance than when another intermediate member is interposed.

Here, the phrase "on the same axis" as used in the present invention encompasses not only cases where the axes match up perfectly, but also cases where the axes are slightly misaligned. In other words, this excludes a configuration in which two members (in this case, the operation component 11 and the drive shaft 30) are structurally offset and linked using another member (such as a roller, a block, or another such intermediate member), but encompasses a configuration in which two members can be considered as being directly coupled and linearly displaced or rotated integrally, using a common axis (in this case, the center axis L0) as a reference axis, and the drive force from the drive shaft 30 is transmitted directly to the operation component 11 without any other member being interposed.

Also, the actuator unit 20 is configured such that an actuator 21 for generating a haptic drive force and a displacement sensor 23 for measuring the amount of displacement of the drive shaft 30 are provided in a substantially cuboid casing 22. The actuator 21 and the displacement sensor 23 are connected to the controller 50, and their drive is controlled by the controller 50 so that a haptic drive force corresponding to the operation of the operation component 11 by the user can be generated. That is, the controller 50 is configured to control the actuator 21 so as to generate a haptic drive force with respect to the amount of displacement of the drive shaft 30, so that a drive force (haptic drive force) corresponding to the tactile feeling experienced by a skilled physician, such as the feeling of a catheter striking the wall of a blood vessel, the feeling of forming a balloon in a blood vessel, and other such light and delicate tactile feelings, can be generated corresponding to the amount of displacement of the drive shaft 30 in the rotation direction and in the center axis L0 direction. Also, the controller 50 is connected to a monitor, and when the displacement amount of the drive shaft 30 is inputted, the same video as when the catheter is actually used in a human body, such as how far the catheter has move into or out of the body according to the displacement amount, or how much the balloon has expanded within the blood vessel, is outputted when the user operates the operation component 11.

The actuator 21 generates a haptic drive force in catheter operation. The actuator 21 has a movable element 24 and a stationary element 25, and these are provided in a state one being inserted into the other. In this embodiment, the actuator 21 is constituted by a shaft motor, and a haptic drive force can be generated by the relative displacement of the movable element 24 and the stationary element 25.

In the present embodiment, the actuator 21 has an axial direction driver 41 for driving the drive shaft 30 in the direction of the center axis L0 and a rotation direction driver 42 for rotationally driving the drive shaft 30 around the center axis L0. The axial direction driver 41 and the rotation direction driver 42 are each controlled so that drive force in the direction of the center axis L0 and drive force in the direction of rotating around the center axis L0 can be generated. In other words, using the controller 50 to control the combination of the directionality of the drive force and the strength of the drive force allows a light and delicate haptic drive force to be generated.

Figure 3:
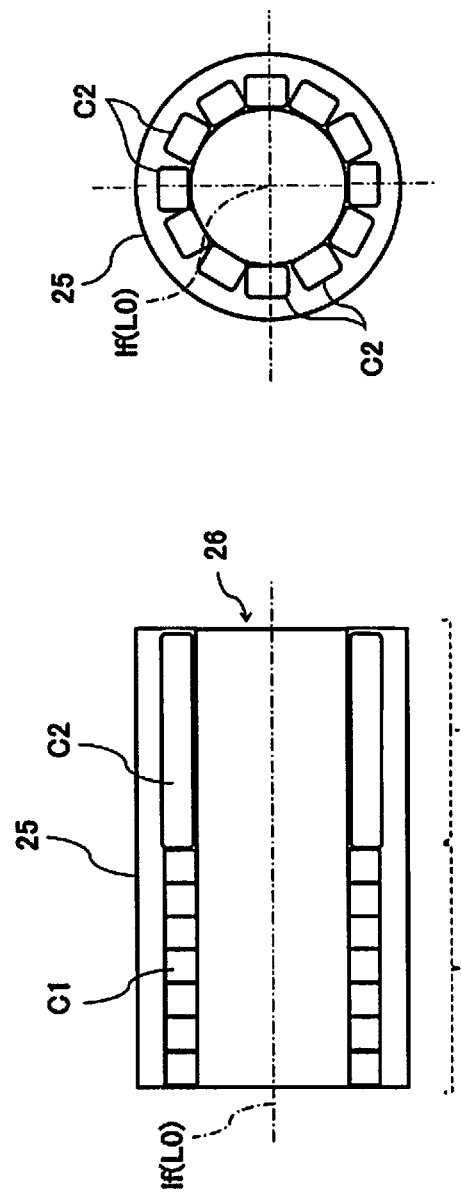
FIGS. 3A and 3B illustrate diagrams of a stationary element in the above embodiment, with FIG. 3A being a cross section viewed from a direction perpendicular to a center axis L0, and FIG. 3B being a cross section viewed from the center axis L0.

The stationary element 25 has a cylindrical shape and is fixed inside the casing 22. More specifically, as shown in FIGS. 3A and 3B, an insertion hole 26 is formed in the center portion of the stationary element 25, and the stationary element 25 is disposed and fixed so that its center axis 1f is located on the same axis (on the center axis L0) as the axes 1s and 1h of the operation component 11 and the drive shaft 30. In this embodiment, the stationary element 25 is formed by an electric coil, and a coil C1 that is wound around the center axis is disposed in the axial direction driver 41. Also, a plurality of electric coils C2 formed by winding are disposed formed around the center axis in a shape that extends along the center axis in the rotation direction driver 42.

The movable element 24 is a rod-shaped member that is inserted into the insertion hole 26 in the stationary element 25. More specifically, the movable element 24 is inserted through an air bearing 27 into the insertion hole 26 of the stationary element 25, and in a state in which it has been inserted, it is not in contact with the stationary element 25, and the center axes 1m and 1f are held in an aligned state. Also, the movable element 24 is linked to the drive shaft 30 and can be displaced with respect to the stationary element 25 in the direction of the center axis 1m and in the rotation direction around the center axis 1m, according to the operation of the operation component 11.

More specifically, the movable element 24 is linked so that its center axis 1m is aligned with the center axis 1s (=L0) of the drive shaft 30, and when the drive shaft 30 is displaced in the center axis L0 direction with the operation component 11, the movable element 24 is displaced in the center axis L0 direction with respect to the stationary element 25, and when the drive shaft 30 is rotated around the center axis L0 with the operation component 11, the movable element 24 rotates around the center axis L0 with respect to the stationary element 25. In other words, the stationary element 25, the movable element 24, and the drive shaft 30 are disposed so that their center axes 1f, 1m, and 1s are on the same axis (on the center axis L0), and the movable element 24 and the drive shaft 30 can be displaced in the axial direction with reference to the center axis L0 and rotate around the axis.

Figure 4:
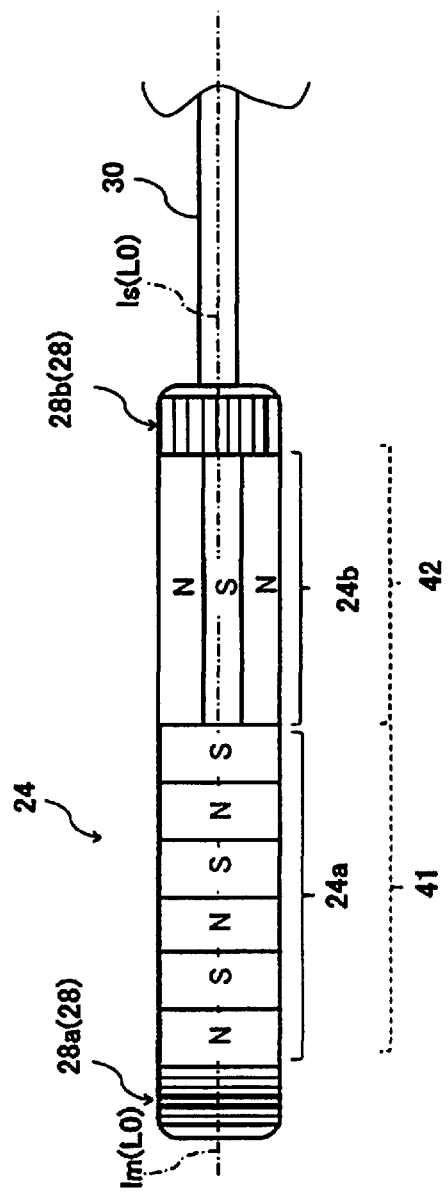
FIG. 4 is a diagram of a movable element in the above embodiment.
Figure 5:
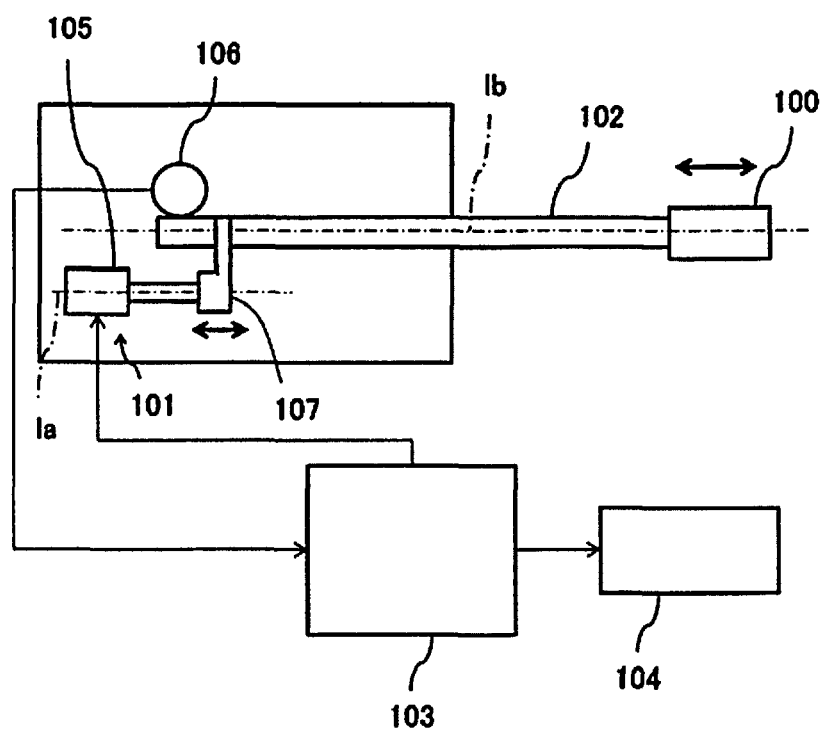
FIG. 5 is a diagram of a conventional operational feeling reproduction device.

Also, the movable element 24 in this embodiment is formed by a permanent magnet. More specifically, as shown in FIG. 4, it has a linear motion magnet component 24a in which the N pole and the S pole are arranged in an alternating pattern in the center axis direction, and rotary magnet component 24b in which the N pole and the S pole are arranged in an alternating pattern around the center axis L0, and these components are disposed in the center axis L0 direction. In a state in which the movable element 24 is inserted through the stationary element 25, the linear motion magnet component 24a is located at the axial direction driver 41 and the rotary magnet component 24b is located at the rotation direction driver 42. Consequently, the movable element 24 can be displaced in the center axis L0 direction by energizing the axial direction driver 41, and the movable element 24 can be displaced around the center axis L0 by energizing the rotation direction driver 42. That is, when the axial direction driver 41 is energized, current flows to the coil C1 to form a current flowing around the center axis L0. Then, the magnetic field formed by the linear motion magnet component 24a causes the movable element 24 to receive thrust in the center axis L0 direction and be displaced in the center axis direction. Also, when the rotation direction driver 42 is energized, current flows to the coil C2 to form a current flowing in the direction along the center axis L0. Then, the rotary magnet component 24b causes the movable element 24 to receive thrust around the center axis L0 and be displaced around the center axis. The controller 50 controls the combination of the direction of these drive forces and the strength of the drive forces, so that a light and delicate haptic drive force is generated in the operation of the catheter.

Also, a line sensor is used as the displacement sensor 23 for measuring the amount of displacement of the drive shaft 30. In this embodiment, it is measured by reading a scale 28 attached to the movable element 24 with a sensor head 23a provided inside the casing 22. More specifically, as shown in FIG. 4, a scale 28a for measuring displacement in the center axis L0 direction and a scale 28b for measuring displacement in the rotation direction around the center axis L0 are attached to the movable element 24, and the amount of displacement of the drive shaft 30 is measured by reading these scales with the sensor head 23a. In this embodiment a line sensor is used, but a linear encoder, a magnetic sensor, or the like may be used instead.

With the operational feeling reproduction device of this embodiment described above, it is possible to accurately transmit the haptic drive force set with the actuator 21, and to obtain a light and delicate tactile feeling. That is, the stationary element 25, the movable element 24, and the drive shaft 30 are disposed so that their central axes $1f$, $1m$, and $1s$ lie on the same axis (on the center axis L0), and the movable element 24 and the drive shaft 30 are configured so that they can be displaced in the axial direction with reference to the center axis L0 and can rotate around the center axis L0, so drive can be performed at a lower resistance, with sliding resistance kept to a minimum, and a haptic drive force adjusted to be the light and delicate haptic drive force a skilled physician would feel can be accurately reproduced. That is, compared to a conventional operational feeling reproduction device in which the center axis of the drive source and the center axis $1s$ of the drive shaft 30 are offset, it is impossible to minimize problems whereby the influence of moment, etc., due to the offset structure, and assembly precision, fitting accuracy, and so forth affect the haptic drive force, and the haptic drive force transmitted to the operation component 11 is slightly shifted.

In the above embodiment, an example was described in which the movable element 24 and the stationary element 25 used a shaft motor (non-contact drive motor), which is a drive source that makes use of magnetic force. However, for applications in which mechanical vibration can be tolerated to some extent, a mechanical drive power source such as a servo motor and a ball screw may be used instead of a shaft motor. Here again, because the center axes $1f$ and $1m$ of the movable element 24 (the block of the ball screw), the stationary element 25 (the base of the ball screw), and the drive shaft 30 lie on the same axis (on the center axis L0), the influence of moment and the like due to the offset structure can be avoided better, and the resulting operational feeling reproduction device can be driven at a lower resistance, in which the sliding resistance is kept to a minimum, as compared to a conventional operational feeling reproduction device with a configuration in which the center axis of the drive source is offset from the center axis is of the drive shaft 30.

Also, in the above embodiment, an example was described in which an electric coil (the stationary element 25) was disposed on the outside diameter side, and a permanent magnet (the movable element 24) was disposed on the inside diameter side, but the disposition of the electric coil and the permanent magnet may be reversed, with the electric coil fixed on the inside diameter side and the permanent magnet disposed on the outside diameter side, and just as above, an electric coil may be used as the stationary element 25, and a permanent magnet on the outside diameter side may be used as the movable element 24, and the stationary element 25 and the movable element 24 may be displaced relative to each other in the center axis direction.

Also, in the above embodiment, an example was described in which the movable element 24 was a permanent magnet and the stationary element 25 was an electric coil. However, the movable element 24 may be an electric coil and the stationary element 25 may be a permanent magnet. That is, regardless of whether the movable element 24 and the stationary element 25 is set, the respective center axes $1f$, $1m$, and $1s$ of the movable element 24, the stationary element 25, and the drive shaft 30 should lie on the same axis (on the center axis L0).

Also, in the above embodiment, an example was described in which the stationary element 25 and the movable element 24 were supported in a non-contact manner by interposing the air bearing 27 between the movable element 24 and the stationary element 25, but in applications where sliding resistance does not need to be kept to an absolute minimum, and a certain amount is allowable, the air bearing 27 may be replaced with a collar or the like having low sliding resistance.

Also, in the above embodiment, an example was described in which the actuator 20 was provided with two actuators 21. However, depending on the application, just one actuator 21 may be provided, or three or more actuators 21 may be provided. That is, no matter how many actuators 21 are used, the movable element 24, the stationary element 25, and the drive shaft 30 should be disposed so that their central axes $1f$, $1m$, and $1s$ lie on the same axis (on the center axis L0).

Also, in the above embodiment, an example was described in which the haptic drive force was generated in the axial direction of the center axis L0 and in the rotation direction around the center axis L0, but depending on the application, the operational feeling reproduction device may drive in only the axial direction of the center axis L0, or only the rotation direction around the center axis L0.

The invention claimed is:
1. An operational feeling reproduction device comprising:
   an operation component configured to be operated by a user;
   an actuator configured to generate a haptic drive force in response to operation of the operation component; and
   a drive shaft coupling the operation component and the actuator, the haptic drive force generated by the actuator being transmitted to the operation component through the drive shaft in response to the operation of the operation component such that an actual operational feeling is experienced, the actuator having a stationary element and a movable element, the actuator being configured to generate the haptic drive force by a relative displacement while one of the stationary element and the movable element is inserted into the other one of the stationary element and the movable element, and the movable element and the operation component being coupled by the drive shaft, center axes of the stationary element, the movable element, and the drive shaft being provided on the same axis.

2. The operational feeling reproduction device according to claim 1, wherein the actuator includes a plurality of actuators, the drive shaft coupled to the movable element of each of the actuators being each coupled to the operation component, each drive shaft shares a common center axis, one drive shaft being inserted into another drive shaft, and the center axes of the drive shaft, and the stationary element and the movable element of each of the actuators are provided on the same axis.

3. The operational feeling reproduction device according to claim 2, wherein the actuator is a non-contact drive motor in which the movable element and the stationary element are relatively displaced in a non-contact manner.

4. The operational feeling reproduction device according to claim 3, wherein the stationary element has an insertion hole through which the movable element is inserted, and the actuator has an air bearing for supporting the movable element relative to the stationary element in a non-contact manner, the air bearing being provided to the insertion hole.

5. The operational feeling reproduction device according to claim 4, wherein the haptic drive force is generated by the actuator in response to an operation of moving the drive shaft along the center axis and an operation of rotating the drive shaft around the center axis.

6. The operational feeling reproduction device according to claim 3, wherein the haptic drive force is generated by the actuator in response to an operation of moving the drive shaft along the center axis and an operation of rotating the drive shaft around the center axis.

7. The operational feeling reproduction device according to claim 2, wherein the stationary element has an insertion hole through which the movable element is inserted, and the actuator has an air bearing for supporting the movable element relative to the stationary element in a non-contact manner, the air bearing being provided to the insertion hole.

8. The operational feeling reproduction device according to claim 7, wherein the haptic drive force is generated by the actuator in response to an operation of moving the drive shaft along the center axis and an operation of rotating the drive shaft around the center axis.

9. The operational feeling reproduction device according to claim 2, wherein the haptic drive force is generated by the actuator in response to an operation of moving the drive shaft along the center axis and an operation of rotating the drive shaft around the center axis.

10. The operational feeling reproduction device according to claim 1, wherein the actuator is a non-contact drive motor in which the movable element and the stationary element are relatively displaced in a non-contact manner.

11. The operational feeling reproduction device according to claim 10, wherein the stationary element has an insertion hole through which the movable element is inserted, and the actuator has an air bearing for supporting the movable element relative to the stationary element in a non-contact manner, the air bearing being provided to the insertion hole.

12. The operational feeling reproduction device according to claim 11, wherein the haptic drive force is generated by the actuator in response to an operation of moving the drive shaft along the center axis and an operation of rotating the drive shaft around the center axis.

13. The operational feeling reproduction device according to claim 10, wherein the haptic drive force is generated by the actuator in response to an operation of moving the drive shaft along the center axis and an operation of rotating the drive shaft around the center axis.

14. The operational feeling reproduction device according to claim 1, wherein the stationary element has an insertion hole through which the movable element is inserted, and the actuator has an air bearing for supporting the movable element relative to the stationary element in a non-contact manner, the air bearing being provided to the insertion hole.

15. The operational feeling reproduction device according to claim 14, wherein the haptic drive force is generated by the actuator in response to an operation of moving the drive shaft along the center axis and an operation of rotating the drive shaft around the center axis.

16. The operational feeling reproduction device according to claim 1, wherein the haptic drive force is generated by the actuator in response to an operation of moving the drive shaft along the center axis and an operation of rotating the drive shaft around the center axis.

* * * * *